(12) United States Patent
Doi et al.

(10) Patent No.: US 7,326,410 B2
(45) Date of Patent: *Feb. 5, 2008

(54) HAIR CONDITIONER COMPOSITIONS

(75) Inventors: Yasuhiro Doi, Wakayama (JP); Takeshi Kaharu, Wakayama (JP); Hiroyuki Masuda, Wakayama (JP); Yoshimasa Okamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/100,604

(22) Filed: Apr. 7, 2005

(65) Prior Publication Data

US 2005/0180941 A1 Aug. 18, 2005

Related U.S. Application Data

(62) Division of application No. 10/211,590, filed on Aug. 5, 2002, now Pat. No. 6,923,954.

(30) Foreign Application Priority Data

Aug. 6, 2001 (JP) .............................. 2001-238101
Apr. 8, 2002 (JP) .............................. 2002-105875

(51) Int. Cl.
*A61Q 5/12* (2006.01)

(52) U.S. Cl. ................ 424/70.19; 424/70.1; 424/70.27

(58) Field of Classification Search ..................... None
See application file for complete search history.

(56) References Cited

U.S. PATENT DOCUMENTS

| 3,449,431 | A |   | 6/1969  | Swenson                  |
|-----------|---|---|---------|--------------------------|
| 4,659,487 | A |   | 4/1987  | May et al.               |
| 5,120,531 | A | * | 6/1992  | Wells et al. ... 424/70.15 |
| 6,146,427 | A |   | 11/2000 | Crutcher                 |
| 6,576,794 | B2|   | 6/2003  | Fukushima et al.         |
| 6,737,050 | B2| * | 5/2004  | Doi et al. ... 424/70.27  |
| 6,923,954 | B2| * | 8/2005  | Doi et al. ... 424/70.19  |

2003/0147822 A1 8/2003 Doi et al.

FOREIGN PATENT DOCUMENTS

| DE | 1 163 850    |    | 2/1964  |
|----|--------------|----|---------|
| DE | 1 950 643    |    | 4/1971  |
| DE | 35 17 098    | A1 | 11/1986 |
| EP | 1 219 290    |    | 7/2002  |
| JP | 58-149378    |    | 9/1983  |
| JP | 06- 178928   |    | 6/1994  |
| WO | WO 88/02985  |    | 5/1988  |
| WO | WO 90/03423  |    | 4/1990  |
| WO | WO 99/28423  |    | 6/1999  |

OTHER PUBLICATIONS

Harry's Cosmeticology by Ralph Harry, pp. 506-512(1982).
European Search Report, Dec. 12, 2002.
Patent Abstract of Japan JP 62-172429 (Jan. 20, 1989).

* cited by examiner

*Primary Examiner*—Jyothsna Venkat
(74) *Attorney, Agent, or Firm*—Oblon, Spivak, McClelland, Maier & Neustadt, P.C.

(57) ABSTRACT

Provided is a conditioner composition, which comprises a tertiary amine represented by the following formula (1):

$$R^1-O-(CH_2)_3-N\begin{matrix}R^2\\|\\R^3\end{matrix} \quad (1)$$

wherein, $R^1$ represents a linear or branched $C_{6-24}$ alkyl or alkenyl group, $R^2$ and $R^3$ are the same or different and each represents a $C_{1-6}$ alkyl group or a group $-(AO)_nH$ (in which A represents a $C_{2-4}$ alkylene group, and n stands for a number of from 1 to 6 with the proviso that n pieces of A are the same or different and are arranged in any order); or a salt thereof. The conditioner composition can impart fiber or hair with good suppleness and smoothness during wetting and after drying and is particularly excellent in imparting hair or fiber with smoothness after drying.

20 Claims, No Drawings

HAIR CONDITIONER COMPOSITIONS

TECHNICAL FIELD

The present invention relates to a conditioner capable of imparting fiber or hair with good suppleness (or flexibility) and smoothness, particularly to a conditioner, when applied to hair, providing good oily feel, suppleness and smoothness from its application until rinsing-off, and also maintaining good suppleness and smoothness even after drying.

RELATED ART

As a conditioner for fiber or hair, a variety of cationic surfactants have so far been employed. When it is used for fiber as a softener, it is required to impart the fiber with soft hand feeling, and when it is used for hair as a hair cosmetic, it is required to impart the hair with oily feel, suppleness and smoothness during wetting of the hair and after drying.

To satisfy such requests, quaternary ammonium salts such as stearyl trimethylammonium chloride, behenyl trimethylammonium chloride and distearyl dimethylammonium chloride have conventionally been used as a conditioner, but they are not satisfactory.

In German Patent DE 3517098, an ether type primary amine is described as a fiber treating agent, and it is described therein that it improves the handling property upon fiber treatment. The description however does not refer to use of such compound as a conditioner and moreover, a primary amine can not bring about sufficient conditioning effects.

In WO90/03423, an ether type tertiary amine having a polyoxyethylene chain is described as a low-temperature detergent, and it is described therein that it effectively removes lipstick or petroleum stains. The description however does not include use of such a compound as a conditioner.

An object of the present invention is therefore to provide a conditioner capable of imparting hair with good suppleness and smoothness during wetting and after drying of the hair, while imparting fiber with good suppleness and touch after drying.

DISCLOSURE OF THE INVENTION

The present inventors have found that a conditioner capable of imparting hair or fiber with good suppleness and smoothness during wetting and after drying, particularly, a conditioner capable of providing excellent smoothness after drying of hair or fiber is available by the use of a specific ether type tertiary amine.

According to the present invention, there is thus provided a conditioner composition, which comprises a tertiary amine represented by the following formula (1):

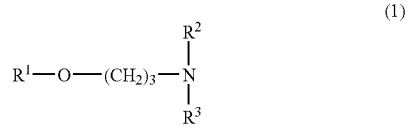

wherein, $R^1$ represents a linear or branched $C_{6-24}$ alkyl or alkenyl group, $R^2$ and $R^3$ are the same or different and each represents a $C_{1-6}$ alkyl group or a group -$(AO)_nH$ (in which A represents a $C_{2-4}$ alkylene group, and n stands for a number of from 1 to 6 with the proviso that n pieces of A may be the same or different and are arranged in any order); or a salt thereof.

BEST MODE FOR CARRYING OUT THE INVENTION

In the above-described formula (1), the below-described groups are preferred as $R^1$, $R^2$ and $R^3$, because these groups can provide good suppleness and smoothness during wetting and after drying of hair or fiber, particularly excellent smoothness after drying of hair or fiber.

As $R^1$, linear or branched $C_{12-24}$, more preferably $C_{14-22}$ alkyl or alkenyl, especially alkyl groups are preferred.

$R^2$ and $R^3$ may be the same or different and each preferably represents a $C_{1-6}$ alkyl group or a group —$(CH_2CH_2O)_n$H wherein n stands for a number of from 1 to 3, especially 1. When either one of $R^2$ and $R^3$ represents a group —$(CH_2CH_2O)_n$H, the other one preferably represents a $C_{1-6}$ alkyl group. It is more preferred that $R^2$ and $R^3$ are the same or different and each represents a $C_{1-6}$ alkyl group, especially methyl or ethyl group.

Various methods for synthesizing a tertiary amine represented by the formula (1) (which will hereinafter referred to as "tertiary amine") are known. It can be prepared, for example, in accordance with the following reaction scheme:

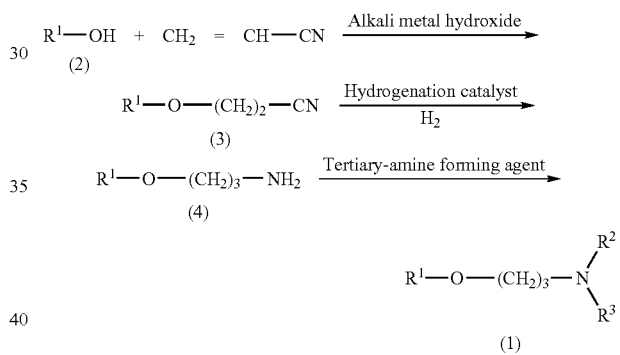

wherein, $R^1$, $R^2$ and $R^3$ have the same meanings as described above.

Specifically, acrylonitrile is reacted with Alcohol (2) in the presence of an alkali metal hydroxide, thereby forming Alkoxypropionitrile (3), followed by hydrogenation by using a hydrogenation catalyst, whereby Alkoxypropylamine (4) is prepared. The resulting Alkoxypropylamine (4) is then reacted with a tertiary-amine forming agent (combination of hydrogen with formaldehyde or an alkyl aldehyde having, in total, 2 to 6 carbon atoms, or a $C_{2-4}$ alkylene oxide) to prepare a tertiary amine.

The conditioner composition of the present invention may contain in addition to the tertiary amine at least one compound selected from inorganic acids and organic acids in order to reduce its amine odor or enhance its conditioning effects such as suppleness and smoothness.

Examples of the inorganic acids include hydrochloric acid, sulfuric acid and phosphoric acid. Examples of the organic acids include monocarboxylic acids such as acetic acid and propionic acid; dicarboxylic acids such as malonic acid, succinic acid, glutaric acid, adipic acid, maleic acid, fumaric acid and phthalic acid; hydroxycarboxylic acids such as glycolic acid, lactic acid, hydroxyacrylic acid, glyceric acid, malic acid, tartaric acid and citric acid; polycarboxylic acids such as polyglutamic acid; and acidic amino acids such as glutamic acid and aspartic acid. Among these acids, inorganic acids, dicarboxylic acids, hydroxycarboxylic acids and acidic amino acids are preferred. As the inorganic acids, hydrochloric acid is especially preferred. As the dicarboxylic acids, maleic acid and succinic acid are especially preferred. As the hydroxycarboxylic acids, glycolic acid, citric acid, lactic acid and malic acid are especially preferred. As the acidic amino acids, glutamic acid is especially preferred.

Addition of the above-described inorganic acid and/or organic acid in an amount of 0.1 to 10 moles, more preferably 0.3 to 3 moles per mole of the tertiary amine or a salt thereof is preferred, because such addition can reduce an amine odor or enhance conditioning effects such as suppleness and smoothness.

When the conditioner composition contains at least one acid selected from inorganic acids and/or organic acids, the tertiary amine may form a salt with these acids or exist without forming a salt.

Examples of the salts of the tertiary amine include salts with the above-described inorganic acids or organic acids. Preferred salts include hydrochlorides, lactates, malates and glutamates.

Although no particular limitation is imposed on the pH of the conditioner composition of the present invention, it is preferably 2 to 8 at 25° C. when diluted to 20-fold with water. Particularly when the conditioner composition is used as a hair rinse or a hair conditioner, pH (at 25° C.) of 3 to 6 is preferred, while pH (at 25° C.) of 5 to 8 is preferred when it is used as a hair shampoo.

In the conditioner composition of the present invention, an oily component can be added further in order to improve hand touch or texture of fiber or touch of hair. Examples of the oily component include hydrocarbons such as higher alcohols, ester oils, silicones, light liquid isoparaffin, light liquid paraffin, paraffin, wax and squalane and glycerides, of which higher alcohols, ester oils and silicones are preferred, with higher alcohols and/or silicones being particularly preferred.

Examples of the higher alcohols include higher alcohols having a linear or branched alkyl or alkenyl group. Of these, preferred are the higher alcohols having a linear or branched $C_{12-26}$ alkyl or alkenyl group, more preferably higher alcohols such as cetanol, cetyl alcohol, stearyl alcohol, arakyl alcohol, behenyl alcohol, carnaubyl alcohol, ceryl alcohol, oleyl alcohol and isostearyl alcohol. Particularly preferred are one or mixtures of two or more of cetanol, cetyl alcohol, stearyl alcohol and behenyl alcohol. The term "cetanol" as used herein means an alcohol composed mainly of cetyl alcohol and containing a higher alcohol such as stearyl alcohol, oleyl alcohol or the like.

As the ester oil, preferred are monoester oils and one or mixtures of two or more of ester oils each having, in the molecule thereof, at least two ester bonds.

Examples of the monoester oil include monoester oils having in total 8 to 40 carbon atoms, preferably monoesters of a monohydric $C_{2-22}$, preferably $C_{8-20}$ fatty acid and a mono- or polyhydric $C_{1-20}$ alcohol. They may be linear or branched, and saturated or unsaturated. Isopropyl palmitate, isopropyl myristate, isononyl isononanoate, triisodecyl isononanoate, stearyl stearate and diglyceryl monoisostearate are especially preferred.

Examples of the polyvalent ester oil having, in the molecule thereof, at least two ester bonds include polyvalent ester oils having in total 8 to 120 carbon atoms, preferably polyvalent ester oils composed of one or more mono- or polyhydric $C_{2-22}$ fatty acids, and one or more mono- or polyhydric $C_{2-20}$ alcohols. They may be linear or branched, saturated or unsaturated, or may further contain an aromatic ring. Particularly preferred are neopentyl glycol dicaprylate, diglyceryl diisostearate and esters of dipentaerythritol with mixed fatty acids such as hydroxystearic acid, stearic acid, rosin and the like.

Examples of the silicones include (A) dimethyl polysiloxane, (B) methylphenyl polysiloxane, (C) amino-modified silicones [aqueous silicone emulsions include "SM8704C" (product of Toray Dow Corning Silicone Co., Ltd.) and "DC939" (product of Toray Dow Corning Silicone Co., Ltd.)], (D) fatty-acid-modified polysiloxanes, (E) alcohol-modified silicones, (F) aliphatic alcohol-modified polysiloxanes, (G) polyether-modified silicones, (H) epoxy-modified silicones, (I) fluorine-modified silicones, (J) cyclic silicones, (K) alkyl-modified silicones, and (L) amino-modified siloxane-polyoxyalkylene block copolymers, which are described in Japanese Patent Laid-Open Publication No. Hei 6-48916.

Among the amino-modified silicones (C), those having hydroxydimethyl or trimethylsilyl termination are preferred. Typical examples thereof include amodimethicone having an average molecular weight of about 3000 to 100000.

The amino-modified silicones (C) are preferably used as an aqueous emulsion. Its aqueous emulsion is available, for example, in accordance with the process as described in Japanese Patent Publication No. Sho 56-38609, by emulsion polymerization of a cyclic diorganopolysiloxane and an organoalkoxysilane having an aminoalkyl group and a hydroxy, hydroxyalkyl, oxyalkylene or polyoxyalkylene group in the presence of a quaternary ammonium salt surfactant and water.

When the amino-modified silicone is used as an aqueous emulsion, its amino-modified silicone content in the emulsion is usually from 20 to 60 wt. %, preferably from 30 to 50 wt. %.

Among the copolymers (L), those represented by the below-described formula are preferred.

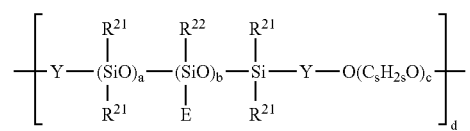

wherein, $R^{21}$ represents a hydrogen atom or a monovalent $C_{1-6}$ hydrocarbon group, $R^{22}$ represents either $R^{21}$ or E, E represents a reactive functional group represented by the formula $R^{23}$-Z (in which $R^{23}$ represents nothing or a divalent $C_{1-20}$ hydrocarbon group and Z represents a primary- to tertiary-amino-containing group or ammonium-containing group), a stands for a number of 2 or greater, b stands for a number of 1 or greater, s stands for a number of from 2 to 10, c pieces of s may be the same or different and each represents a number of 4 or greater, d stands for a number of 2 or greater, and Y represents a divalent organic group which has been bonded to an adjacent silicon atom via a carbon-silicon atom and to a polyoxyalkylene block chain via an oxygen atom, with the proviso that a plural pieces of each of $R^{21}$, $R^{22}$ and E may be the same or different.

Among these silicones, the above-described (A), (C), (F), (G), (J) and (L) are preferred when the conditioner composition of the present invention is a rinse-off type hair cosmetic composition such as hair rinse or hair conditioner, while the above-described (A), (B), (C), (G), (J) and (L) are preferred when the conditioner composition is not a rinse-off type hair cosmetic composition such as hair cream or leave-on treatment.

The content of the tertiary amine or a salt thereof in the conditioner composition of the present invention is preferably from 0.01 to 30 wt. %, more preferably 0.1 to 20 wt. %, still more preferably from 0.1 to 10 wt. %, especially from 0.5 to 10 wt. %, because within this range, the resulting conditioner composition can impart hair or fiber with sufficient suppleness and smoothness and moreover, is free from precipitation, solidification, layer separation, etc. upon storage and thus stable as a product. The content of the oily component is preferably from 0.01 to 30 wt. %, more preferably from 0.1 to 30 wt. %, especially from 1 to 20 wt. %, because within this range, the resulting conditioner composition can impart hair or fiber with sufficient suppleness and moisturized feeling peculiar to the oily component and moreover, it is stable as a product. Among the oily components, the content of the silicone is preferably from 0.01 to 20 wt. %, especially from 0.1 to 10 wt. %, because within this range, the resulting conditioner composition can provide hair or fiber with sufficient touch peculiar to the silicone and is stable as a product.

In the conditioner composition of the present invention, the weight ratio of the tertiary amine or a salt thereof (the "tertiary amine or a salt thereof" will hereinafter be called "tertiary amine") to the oily component is, as a tertiary amine/oily component ratio, preferably from 20/1 to 1/30, more preferably from 10/1 to 1/10, especially from 1/1 to 1/10 from the viewpoint of the emulsion stability of the oily component. The weight ratio of the sum of the tertiary amine and the oily component other than the silicone to the silicone is, as [tertiary amine+oily components other than silicone]/silicone, preferably from 20/1 to 1/20, more preferably from 10/1 to 1/10, especially from 10/1 to 1/5 in view of stability of the product.

The conditioner composition of the present invention can further contain a quaternary ammonium salt in order to impart fiber or hair with coating touch and to enhance rich feel synergistically. Examples thereof include quaternary ammonium salts represented by the following formula (5):

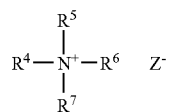

(5)

wherein, at least one of $R^4$, $R^5$, $R^6$ and $R^7$ represents a linear or branched alkyl or alkenyl group which may be substituted by an alkoxy, alkenyloxy, alkanoylamino, alkenoylamino, alkanoyloxy or alkenoyloxy group and has, in total, 12 to 28 carbon atoms, preferably 16 to 28 carbon atoms, while the remaining group(s) represent a benzyl group, a $C_{1-5}$ alkyl group, a hydroxyalkyl group, or a polyoxyethylene group whose added molar number is not more than 10 in total, $Z^-$ represents a halogen ion or an organic anion, for example, selected from acetate, citrate, lactate, glycolate, phosphate, nitrate, sulfonate, sulfate and alkylsulfate].

The compound (5) is preferably a monoalkyltrimethylammonium chloride which may be substituted by an alkoxy group or a dialkyldimethylammonium chloride which may be substituted by an alkoxy group, and is more preferably a $C_{16-22}$ monoalkyltrimethylammonium chloride which may be substituted by an alkoxy group, for example, cetyltrimethylammonium chloride, stearyltrimethylammonium chloride, behenyltrimethylammonium chloride, cetyloxypropyltrimethylammonium chloride or stearyloxypropyltrimethylammonium chloride.

The ratio of the tertiary amine to the quaternary ammonium salt to be used in the present invention is, as "tertiary amine/quaternary ammonium salt" (weight ratio), preferably not less than 1/4, more preferably from 1/2 to 20/1, especially from 1/1 to 10/1.

Furthermore, the conditioner composition of the present invention may contain, within an amount not impairing the object of the present invention, another surfactant such as cationic surfactant, anionic surfactant, nonionic surfactant or amphoteric surfactant; another hydrocarbon; a lanolin derivative; another higher fatty acid ester; a higher fatty acid: another oil or fat; an ether oil such as isostearyl glyceryl ether or isostearyl pentaerythryl glyceryl ether; a fluorinated oil such as fluorinated hydrocarbon, fluoroester or fluoroether; a moisturizer such as glycerin, ceramide, pseudoceramide, hyaluronic acid, polyethylene glycol having a molecular weight of not less than 300, polypropylene glycol having a molecular weight of more than 5000 or polyglycerin; a cationic polymer; a polysaccharide: a polypeptide such as hydrolyzed silk or collagen; a pearling agent, for example, an organic pearling agent such as ethylene glycol distearate or distearyl ether, or an inorganic pearling agent such as mica-titanium; a liquid-crystal forming material; an aromatic sulfonic acid or salt thereof such as naphthalenesulfonic acid or salt thereof; a colorant such as acid dye, basic dye or pigment; a perfume; a propellant; a chelating agent such as EDTA; a pH regulator, for example, a base such as NaOH, KOH or triethanolamine, or an acid; an antiseptic such as paraben, benzoic acid or methylchloroisothiazolinone; antidandruff (amount of the antidandruff is preferably from 0.01 to 1 wt. %) such as zinc pyrithione, piroctone olamine or sulfur; an ultraviolet absorber such as cinnamic acid derivative, benzophenone derivative or paraminobenzoic acid derivative; an antioxidant such as BHT, BHA or tocopherol, an antibacterial agent such as triclosan or trichlorocarbanilide; an animal or vegetable oil such as olive oil or jojoba oil; another amino acid; a vitamin or provitamin such as pantenol; an inorganic or organic insoluble powder; a viscosity regulator such as clay mineral; a plant extract; a hair growth tonic; an anti-inflammatory agent; and/or a cool feeling agent such as menthol.

Examples of the cationic surfactant include acid-neutralized products of an amidoamine compound represented by the following formula (6):

(6)

(wherein, $R^8$ represents a residue of a $C_{11-21}$ higher fatty acid, $R^9$ represents a $C_{1-4}$ alkyl or hydroxyalkyl group, and t stands for an integer of from 2 to 4). Examples of the acid used for neutralization include inorganic acids such as hydrochloric acid and phosphoric acid, organic acids such as citric acid, lactic acid and malic acid, and acidic amino acids such as glutamic acid and α-alanine. Specific examples of the acid-neutralized amidoamine compound include stearic dimethylaminopropylamide hydrochloride, stearic diethylaminoethylamide glutamate, and behenic dimethylaminopropylamide malate. The amidoamine compound is added preferably in an amount of from 0.01 to 20 wt. %, more preferably from 0.05 to 10 wt. % based on the conditioner composition.

As the anionic surfactant, sulfuric acid, sulfonic acid, carboxylic acid, phosphoric acid or amino acid surfactants are preferred. Examples include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkyl phenyl ether sulfates, alkane sulfonates, acyl isethionates, acyl methyl taurates, higher fatty acid salts, polyoxyalkylene alkyl ether acetates, alkyl phosphates, polyoxyalkylene alkyl ether phosphates, acyl glutamates, alanine derivatives, glycine derivatives and arginine derivatives.

Among these anionic surfactants, preferred are polyoxyethylene alkyl ether sulfates, polyoxyethylene alkenyl ether sulfates, alkyl sulfates, acyl isethionate, acyl methyl taurate, higher fatty acid salts, polyoxyalkylene alkyl ether acetates, alkyl phosphates, polyoxyalkylene alkyl ether phosphates, acyl glutamates and alkyl alanine derivatives, of which the compounds represented by the below-described formula (7) or (8) are preferred.

  (7)

  (8)

(wherein, $R^{10}$ represents a $C_{10-18}$ alkyl or alkenyl group, $R^{11}$ represents a $C_{10-18}$ alkyl group, M represents an alkali metal, alkaline earth metal, ammonium, alkanolamine or basic amino acid, and m stands for an average number of mole of ethylene oxide added, specifically, 1 to 5). The amount of the anionic surfactant is preferably from 0.01 to 30 wt. %, more preferably from 0.05 to 20 wt. % based on the conditioner composition.

Examples of the nonionic surfactant include fatty acid alkanol amides such as polyoxyalkylene sorbitan fatty acid esters, sorbitan fatty acid esters, glycerin fatty acid esters, polyoxyalkylene glycerin fatty acid esters, polyoxyalkylene alkyl ethers, palm kernel fatty acid methylmethanolamide and coconut fatty acid methylethanolamide, polyoxyethylene hydrogenated castor oil and alkyl polyglucosides. The nonionic surfactant is added preferably in an amount of from 0.01 to 30 wt. %, more preferably from 0.05 to 20 wt. %, based on the conditioner composition.

As the amphoteric surfactant, preferred are fatty acid amidopropylbetaines, and more specifically, coconut fatty acid amidopropylbetaine, lauric acid amidopropylbetaine and alkyldimethylamine oxides. The amphoteric surfactant is added preferably in an amount of from 0.01 to 30 wt. %, more preferably from 0.05 to 20 wt. % based on the conditioner composition.

In the conditioner composition of the present invention, the above-described cationic polymers may be incorporated as a thickener or touch improver. Various synthetic polymers such as cationized cellulose, cationized guar gum and a copolymer of diallyldimethylammonium chloride and acrylamide can be given as examples of the cationic polymer. The cationic polymer is added preferably in an amount of from 0.01 to 20 wt. %, especially from 0.05 to 15 wt. % based on the conditioner composition.

In the conditioner composition of the present invention, a thickening polymer may be incorporated further. Examples of the thickening polymer include hydroxyethyl cellulose, guar gum, xanthan gum and polyacrylic acid polymers. The amount of the thickening polymer is preferably from 0.01 to 20 wt. %, especially from 0.05 to 15 wt. %, based on the conditioner composition.

In order to improve hair styling ease and touch, a film forming polymer may be added to the composition. Examples thereof include polyvinyl pyrrolidone polymer compounds such as polyvinyl pyrrolidone, vinyl pyrrolidone/vinyl acetate copolymer, and vinyl pyrrolidone/dialkylaminoethyl methacrylate (quaternary salt) copolymer; acid vinyl ether polymer compounds such as methyl vinyl ether/maleic anhydride alkyl half ester copolymer; acid acrylic polymer compounds such as (meth)acrylic acid/(meth)acrylate copolymer, acrylic acid/alkyl acrylate/alkylacrylamide copolymers; amphoteric acrylic polymer compounds such as N-methacryloylethyl-N,N-dimethylammonium.α-N-methylcarboxybetaine/butyl methacrylate copolymer; basic acrylic polymer compounds such as acrylamide.acrylate quaternary copolymers; and chitin.chitosan derivatives such as hydroxypropyl chitosan, carboxymethyl chitin and carboxymethyl chitosan.

Two or more of these film forming polymers may be used in combination and their content may preferably range from 0.1 to 10%, especially from 0.5 to 5%.

The conditioner composition of the present invention may further contain an organic solvent, other than the above-described moisturizer, selected from the following compounds (1) to (5):

(b-1) compounds represented by the formula (9)

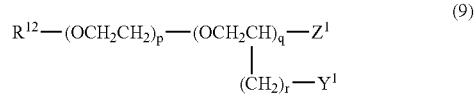  (9)

wherein, $R^{12}$ represents a hydrogen atom, a lower alkyl group or a group $R^{13}$-Ph-$R^{14}$— ($R^{13}$; hydrogen atom, methyl group or methoxy group, $R^{14}$; a free valence bond or a saturated or unsaturated divalent $C_{1-3}$ hydrocarbon group, Ph; paraphenylene group), $Y^1$ and $Z^1$ each represents a hydrogen atom or a hydroxyl group, and p, q and r each stands for an integer of from 0 to 3, with the proviso that when p=q=0, $Z^1$ does not represent a hydrogen atom and $R^{12}$ represents neither a hydrogen atom nor a group $R^{13}$-Ph-, and that the above-described moisturizer is excluded.

(b2) N-alkyl pyrrolidones having a $C_{1-18}$ alkyl group attached to the nitrogen atom, (b3) $C_{1-4}$ alkylene carbonates, (b4) polypropylene glycol having a molecular weight of from 200 to 5000, and (b5) lactone or cyclic ketones represented by the following formula (10), (11) or (12):

  (10)

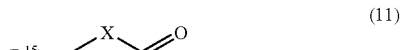  (11)

  (12)

wherein, X represents a methylene group or an oxygen atom, $R^{15}$ and $R^{16}$ respectively represent substituents which are different from each other, and e and f each stands for 0 or 1].

Among the above-described organic solvents, examples of the compound (b1) include ethanol, 1-propanol, 2-propanol, butanol, isobutanol, ethylene glycol, propylene glycol, 1,3-butanediol, benzyl alcohol, cinnamyl alcohol, phenethyl alcohol., p-anisyl alcohol, p-methylbenzyl alcohol, phenoxyethanol, 2-benzyloxyethanol, methyl carbitol, ethyl carbitol, propyl carbitol, butyl carbitol, triethylene glycol monoethyl ether, triethylene glycol monobutyl ether and glycerin. Examples of the (b2) include N-methyl pyrrolidone, N-octyl pyrrolidone and N-lauryl pyrrolidone. Examples of the (b3) include ethylene carbonate and propylene carbonate. As the propylene glycol (b4), those having a molecular weight of from 200 to 1000 are preferred. In the compound (b5), preferred as $R^{15}$ or $R^{16}$ of the formulas (10) to (12) are linear, branched or cyclic alkyl groups, hydroxyl groups, sulfonic acid groups, phosphoric acid groups, carboxy groups, phenyl group, sulfoalkyl groups, phosphoric acid alkyl groups, and carboxyalkyl groups. In the case of γ-lactone or δ-lactone, linear or branched $C_{1-6}$ alkyl groups such as methyl, ethyl, propyl, isopropyl or butyl group substituted at the γ-position or δ-position (that is, methylene adjacent to the hetero oxygen atom), respectively are preferred. When increase of the water solubility of the compound represented by any one of the formulas (10) to (12) is desired, it is preferred to have, as $R^{15}$ or $R^{16}$, an acid group such as sulfonic acid group, phosphoric acid group, or carboxyl group, or an alkyl group substituted with the acid group. When the compound (b5) is a lactone, examples thereof include γ-butyrolactone, γ-caprolactone, γ-valerolactone, δ-caprolactone and δ-heptanolactone. In view of the stability of lactone, γ-lactone, especially, γ-butyrolactone and γ-caprolactone are preferred. When the compound (b5) is a cyclic ketone, examples thereof include cyclopentanone, cyclohexanone, cycloheptanone and 4-methylcycloheptanone.

Two or more of these organic solvents may be used in combination. From the viewpoint of improving the feeling upon use, luster and suppleness, the content of the organic solvent is preferably from 0.01 to 50 wt. %, more preferably from 0.1 to 35 wt. %, especially from 0.5 to 10 wt. % based on the hair shampoo of the present invention.

The conditioner composition of the present invention may be provided in a desired form such as aqueous solutions, ethanol solutions, emulsions, suspensions, gels, liquid crystals, solids, aerosols, or sprays.

When used for hair, the conditioner of the present invention can be provided as a product such as hair rinse, hair conditioner, hair treatment, hair pack, hair cream, conditioning mousse (conditioning foam), hair mousse (hair foam), hair spray, shampoo, leave-on treatment, wax, tonic or hair lotion. When used for fiber, it can be provided as a product such as fiber softener or fiber finishing product. Among these products, preferred is a hair cosmetic composition, especially a hair rinse, hair conditioner or hair treatment each containing, in addition to water as a medium, 0.1 to 10 wt. % of the tertiary amine or salt thereof of the present invention. When the conditioner of the present invention is used for a shampoo, a clear shampoo capable of imparting hair with excellent conditioning effects is obtained.

EXAMPLES

A description will next be made of Preparation Examples and Examples, in which all designations of "%" and "ppm" are by weight. The reagent and catalyst used in the tests were industrially available products or prepared therefrom. Formalins used in the tests all contain 36% formaldehyde, 57% water and 7% methanol. The pH in these examples was measured at 25° C. after 20-fold dilution with water.

Preparation Example 1 (Preparation of Amine 1)

In a flask were charged a 35:65 (%) mixture of 1-hexadecanol and 1-octadecanol as a higher alcohol and potassium hydroxide, followed by heating to 120° C. and dehydration in the reaction system for 1 hour. After completion of the dehydration, the mixture was cooled to 60° C., to which acrylonitrile was added dropwise over 1 hour. After dropwise addition, stirring was conducted at the same temperature for 30 minutes, whereby an aimed cyanoethylated alcohol was obtained.

In a 2L autoclave were charged the cyanoethylated alcohol thus obtained, a Raney nickel catalyst, water and sodium hydroxide. After purging with hydrogen, the pressure and temperature of the reaction system were raised to 2.0 Mpa and 120° C., respectively. The reaction was effected maintaining the pressure at 2.0 Mpa. When the hydrogen absorption amount became 0, the reaction was terminated. After aging for 30 minutes, the reaction mixture was cooled to 80° C. and then filtered to remove therefrom the catalyst, whereby an aimed 3-hexadecyloxypropylamine/3-octadecyloxypropylamine mixture was obtained.

In a 2L autoclave were charged the 3-hexadecyloxypropylamine/3-octadecyloxypropylamine mixture and 5% Pd/C catalyst (water content: 50%), followed by purging with hydrogen. After heating to 120° C., the pressure and discharge flow rate (flow rate at the outlet of the autoclave) were controlled to 2.0 Mpa and 5 L/h, respectively, by using hydrogen. While stirring, formalin (2.2 times the mole) was fed continuously over 5 hours. In order to make up for the loss of hydrogen due to absorption by the reaction, hydrogen was fed to maintain the pressure at 2.0 Mpa. After the feeding of formalin was completed, aging was conducted for 30 minutes, whereby the reaction was completed. After cooling, the reaction mixture in the slurry form was taken out from the autoclave. The reaction mixture was filtered (through a 5 C filter paper) and then, the filtrate was allowed to stand to separate into layers. The upper layer (oil layer) was taken out.

The upper layer was then purified by removing, under reduced pressure, remaining low-boiling-point substances such as water, methanol and formaldehyde, whereby an aimed N,N-dimethyl-3-hexadecyloxypropylamine/N,N-dimethyl-3-octadecyloxypropylamine mixture (Amine 1) was obtained.

Preparation Example 2 (Preparation of Amine 2)

In a similar manner to that employed for preparation of Amine 1 except for use of a 35:65 mixture of 1-tetradecanol/1-hexadecanol as the raw material higher alcohol and, instead of formalin, acetaldehyde, Amine 2 was prepared.

Preparation Example 3 (Preparation of Amine 3)

In a similar manner to that employed for preparation of Amine 1 except for use of 1-octadecanol as the raw material higher alcohol, Amine 3 was prepared.

Preparation Example 4 (Preparation of Amine 4)

In a similar manner to that employed for preparation of Amine 1 except for the use of a 4:12:82:2 (%) mixture of $C_{18}$, $C_{20}$, $C_{22}$ and $C_{24}$ alcohols as the raw material higher alcohol, Amine 4 was prepared.

Example 1

By using Amines 1 to 4 shown in Table 1 and, for comparison, conventional cationic surfactants, hair rinses (Invention Products 1 to 9, Comparative Products 1 to 3) having the compositions as shown in Table 2 were prepared in a manner known per se in the art. Their suppleness and smoothness were evaluated by sensory evaluation in the below-described method. The numerical values in Table 2 are all by "wt. %".

TABLE 1

| Tertiary amine | Formula (I) $R^1$ (all, linear) | $R^2$ | $R^3$ | Purity |
|---|---|---|---|---|
| Amine 1 | $C_{16}H_{33}/C_{18}H_{37}$ = 35/65 (%) | $CH_3$ | $CH_3$ | 91% (the remaining portion: unreacted higher alcohol, alkyl primary amine, dialkylamine, etc.) |
| Amine 2 | $C_{14}H_{29}/C_{16}H_{33}$ = 35/65 (%) | $C_2H_5$ | $C_2H_5$ | 88% (the remaining portion: unreacted higher alcohol, alkyl primary amine, dialkylamine, etc.) |
| Amine 3 | $C_{18}H_{37}$ | $CH_3$ | $CH_3$ | 94% (the remaining portion: unreacted higher alcohol, alkyl primary amine, dialkylamine, etc.) |
| Amine 4 | $C_{18}H_{37}/C_{20}H_{41}/C_{22}H_{45}/C_{24}H_{49}$ = 4/12/82/2 (%) | $CH_3$ | $CH_3$ | 90% (the remaining portion: unreacted higher alcohol, alkyl primary amine, dialkylamine, etc.) |

<Evaluation Method>

The hair (weight: 20 g, length: 20 cm) of a Japanese female subject preliminarily treated with a cold permanent was bundled and was shampooed with a commercially available shampoo composed mainly of an anionic surfactant. To the hair, 1.0 g of each of the hair rinses was uniformly applied, followed by rinsing with running water of 40° C. for 30 seconds.

Rich feel upon application, suppleness and smoothness of the hair during rinsing and suppleness and smoothness of the hair after sufficient drying by a drier after towel drying were evaluated by 5 expert panelists in accordance with the following criteria:

4: excellent, 3: good, 2: neither good nor bad, 1: bad.

The average of evaluation scores of five panelists was calculated. The average score was evaluated as follows: not less than 3.6 as A, from 2.6 to 3.4 as B, from 1.6 to 2.4 as C, and not more than 1.6 as D. The results are shown in Table 2.

TABLE 2

| Hair rinse composition (%) | Invention products | | | | | | | | | Comparative products | | |
|---|---|---|---|---|---|---|---|---|---|---|---|---|
| | 1 | 2 | 3 | 4 | 5 | 6 | 7 | 8 | 9 | 1 | 2 | 3 |
| Amine 1 | 1.5 | | | | | | | | | | | |
| Amine 2 | | 1.2 | 1.2 | | | | | | | | | |
| Amine 3 | | | | 1.8 | 1.0 | | 1.5 | | 0.9 | | | |
| Amine 4 | | | | | | 0.5 | | 1.0 | | | | |
| Stearyloxypropylamine | | | | | | | | | | | | 1.8 |
| Cetyltrimethylammonium chloride | | | | | | 0.5 | | | | 1.5 | 1.1 | |
| Behenyltrimethylammonium chloride | | | 0.5 | | | | | 0.2 | 0.8 | | | |
| 35% aq. soln. of hydrochloric acid (molar ratio relative to amine) | | 0.2 (0.6) | 0.2 (0.6) | | | | | | | | | |
| 90% aq. soln. of lactic acid (molar ratio relative to amine) | 0.35 (0.9) | 0.2 (0.7) | 0.2 (0.7) | 0.6 (1.3) | | 0.1 (1.9) | | | 0.2 (0.8) | 0.35 | | 0.7 (1.3) |
| Glutamic acid (molar ratio relative to amine) | | | | | 0.3 (0.8) | | | | | | | |
| Maleic acid (molar ratio relative to amine) | | | | | | | 0.5 (1.3) | | | | | |
| Malic acid (molar ratio relative to amine) | | | | | | | | 0.2 (0.7) | | | | |
| Cetanol 1 | 3.0 | 3.5 | 3.5 | 5.0 | 3.5 | 2.0 | 4.0 | 3.5 | 3.5 | 3.0 | 2.0 | 5.0 |
| Behenyl alcohol | | | | | | 1.0 | | | | | 1.0 | |
| Methyl polysiloxane (500 cs) | 1.0 | | | 1.5 | | 2.0 | 1.0 | | 2.0 | 1.0 | 2.0 | 1.5 |
| Isopropyl palmitate | | | | | | | | | 1.0 | | | |
| Purified water | Balance | Balance | Balance | Balance | Balance | Balance | Balance | Balance | Balance | Balance | Balance | Balance |
| PH regulator | q.s. | q.s. | q.s. | q.s. | q.s. | q.s. | q.s. | q.s. | q.s. | q.s. | q.s. | q.s. |
| Total | 100.00 | 100.00 | 100.00 | 100.00 | 100.00 | 100.00 | 100.00 | 100.00 | 100.00 | 100.00 | 100.00 | 100.00 |
| PH | 4.5 | 3.5 | 3.5 | 4.0 | 5.0 | 4.0 | 4.0 | 4.5 | 4.0 | 4.5 | 4.0 | 4.0 |

TABLE 2-continued

|  |  | Invention products | | | | | | | | | Comparative products | | |
|---|---|---|---|---|---|---|---|---|---|---|---|---|---|
| Hair rinse composition (%) | | 1 | 2 | 3 | 4 | 5 | 6 | 7 | 8 | 9 | 1 | 2 | 3 |
| Evaluation results | | | | | | | | | | | | | |
| When wet, | rich feel | A | B | A | A | B | A | B | A | A | C | C | D |
|  | suppleness | A | A | A | A | A | B | A | A | B | D | D | C |
|  | smoothness | B | B | B | A | B | B | A | B | A | D | C | B |
| After dry, | suppleness | B | A | A | A | B | B | B | B | A | D | C | C |
|  | smoothness | A | B | B | A | B | A | A | B | A | C | B | B |

Cetanol 1 is a 7:3 (weight ratio) mixture of cetyl alcohol and stearyl alcohol, which will equally apply hereinafter.

Example 2

A hair treatment having the below-described composition was prepared.

|  | (wt. %) |
|---|---|
| Amine 1 | 3.0 |
| A 90% aq. soln. of lactic acid | 1.5 |
| Stearyl alcohol | 3.1 |
| Isopropyl palmitate | 1.0 |
| Methyl polysiloxane (500 cs)* | 0.5 |
| Propylene glycol | 3.5 |
| Hydroxyethyl cellulose | 0.5 |
| Ethanol | 2.0 |
| PH regulator | q.s. |
| Perfume, methyl paraben | q.s. |
| Purified water | balance |
| Total | 100.0 |

*"SH200C 500 cs"; product of Toray Dow Corning Silicone Co., Ltd.

The hair treatment thus prepared had a pH of 3.5 and was good in oily feel, suppleness and smoothness from its application until rinsing, and also in suppleness and smoothness after drying.

Example 3

A hair treatment having the below-described composition was prepared.

|  | (wt. %) |
|---|---|
| Amine 3 | 2.5 |
| A 35% aq. soln. of hydrochloric acid | 0.7 |
| Cetanol 1 | 6.5 |
| Dimethyl polysiloxane (100000 cs)* | 4.0 |
| Propylene glycol | 5.0 |
| Hydroxyethyl cellulose | 0.3 |
| PH regulator | q.s. |
| Perfume, methyl paraben | q.s. |
| Purified water | Balance |
| Total | 100.0 |

*"SH200, 100000 cs"; product of Toray Dow Corning Silicone Co., Ltd.

The hair treatment thus prepared had a pH of 3.5 and was good in oily feel, suppleness and smoothness from its application until rinsing, and also in suppleness and smoothness after drying.

Example 4

A hair rinse having the below-described composition was prepared.

|  | (wt. %) |
|---|---|
| Amine 4 | 0.8 |
| A 90% aq. soln. of lactic acid | 0.2 |
| Cationized cellulose* | 0.2 |
| Cetanol 1 | 3.0 |
| Diethylene glycol monoethyl ether | 5.0 |
| Isopropyl myristate | 1.0 |
| PH regulator | q.s. |
| Perfume, methyl paraben | q.s. |
| Purified water | Balance |
| Total | 100.0 |

*"JR400", product of UCC

The hair rinse thus prepared had a pH of 4.5 and was good in oily feel, suppleness and smoothness during from its application until rinsing and also in suppleness and smoothness after drying.

Example 5

Hair shampoos (Invention products 10 and 11, and Comparative products 4 and 5) each having the composition as shown in Table 3 were prepared in a manner known per se in the art. These shampoos were evaluated for feeling upon use and low-temperature stability in accordance with the below-described methods. The numerical values in Table 3 are all by "wt. %".

<Evaluation Method>

The hair (weight: 20 g, length: 20 cm) of a Japanese female subject preliminarily treated with a cold permanent was bundled. To the bundle, 1 g of each of the hair shampoos was applied. After foaming for 30 seconds, rinsing and towel drying, the hair was dried by a drier. The hair shampoo was evaluated for quality of the foam, touch upon shampooing, and touch and manageability of the hair after drying by 5 expert panelists in accordance with the below-described criteria.

4: excellent, 3: good, 2: neither good nor bad, 1: bad

The average of evaluation scores of five panelists was calculated. The average score was evaluated as follows: not less than 3.6 as A, from 2.6 to 3.4 as B, from 1.6 to 2.4 as C, and not more than 1.6 as D.

(Low-Temperature Stability)

The hair shampoo (50 g) was charged in a 3 cm (inner diameter)×7.5 cm (height) glass bottle with a plastic cover.

The bottle was sealed and allowed to stand at 0° C. for 24 hours. The appearance was evaluated in accordance with the following criteria:

A: Transparent without no change in appearance.

B: Turbidity or precipitation is observed.

The evaluation results of feeling upon use (foam quality, touch upon shampooing, touch and manageability of the hair after drying) and low-temperature stability are shown in Table 3.

TABLE 3

| Composition of hair shampoo (%) | Invention product | | Comparative product | |
|---|---|---|---|---|
| | 10 | 11 | 4 | 5 |
| Amine 1 | 0.5 | | | |
| Amine 3 | | 0.5 | | |
| Cetyltrimethylammonium chloride | | | 0.5 | |
| Behenyltrimethylammonium chloride | | | | 0.1 |
| 90% aq. soln. of lactic acid (relative to amine, molar ratio) | 0.2 (1.5) | 0.2 (1.5) | 0.2 | 0.2 |
| Sodium polyoxyethylene (3) lauryl ether sulfate | 15.0 | 15.0 | 15.0 | 15.0 |
| Lauryl diethanolamide | 2.0 | 2.0 | 2.0 | 2.0 |
| Coconut oil amidopropylbetaine | 0.5 | | 0.5 | 0.5 |
| Hydroxysulfobetaine | | 0.7 | | |
| Cationic polymer* | 0.2 | 0.2 | 0.2 | 0.2 |
| PH regulator | q.s. | q.s. | q.s. | q.s. |
| Purified water | Balance | Balance | Balance | Balance |
| Total | 100.00 | 100.00 | 100.00 | 100.00 |
| PH | 6.5 | 7.0 | 6.5 | 6.5 |
| Evaluation results | | | | |
| Quality of foam | B | B | C | B |
| Touch upon shampooing | B | A | C | D |
| Touch after drying | A | A | D | D |
| manageability of hair | B | B | C | D |
| Low-temperature stability | B | B | D | B |

*"Merquat 550" trade name, product of Calgon.

The hair shampoos according to the present invention exhibit good conditioning effects, and are transparent even at low temperatures, thus having excellent stability.

Examples 6 and 7

Hair treatments having the compositions as shown in Table 4 were prepared.

TABLE 4

| | (wt. %) | |
|---|---|---|
| | Example 6 | Example 7 |
| Amine 3 | 2.50 | 2.50 |
| 90% aq. soln. of lactic acid | 0.70 | 0.70 |
| Stearyl alcohol | 4.00 | 4.00 |
| Behenyl alcohol | 1.00 | 1.00 |
| Highly polymerized dimethylpolysiloxane (viscosity: 10 million cp) | 0.40 | 0.40 |
| Dimethylpolysiloxane (viscosity: 500 cs) | 1.60 | 1.60 |
| Aminoethylaminopropylmethylsiloxane-dimethylsiloxane copolymer (viscosity: 1000 cs, amino equivalent: 2000) | 0.10 | — |
| Amino-modified polysiloxane-polyoxyalkylene block copolymer* | — | 0.10 |
| Isopropyl palmitate | 1.00 | 1.00 |
| Dipentaerythrit fatty acid ester** | 0.50 | 0.50 |
| Olive oil | 0.10 | 0.10 |
| Stearyl dimethylaminopropylamide | 0.10 | 0.10 |
| Behenyltrimethylammonium chloride | 0.30 | 0.30 |
| Propylene glycol | 2.00 | 2.00 |
| Benzyloxyethanol | 0.20 | 0.20 |
| Highly polymerized polyethylene glycol*** | 0.05 | 0.05 |
| BHT | 0.01 | 0.01 |
| PH regulator (adjusting pH 3.5 to 4.0) | q.s. | q.s. |
| Perfume, colorant, methyl paraben | q.s. | q.s. |
| Purified water | Balance | Balance |
| Total | 100.00 | 100.00 |

*"FZ-3789" (product of Nippon Unicar)
**"Cosmol 168AR" (product of The Nisshin Oil Mills, Ltd.)
***"POLYOX WSR-N60K (product of Dow Chemical Japan)

The hair treatments thus prepared were good in oily feel, suppleness and smoothness from its application until after rinsing, and suppleness and smoothness after drying.

Example 8

A hair rinse having the following composition was prepared.

| | (wt. %) |
|---|---|
| Amine 3 | 1.50 |
| Glutamic acid | 0.10 |
| 90% Aq. soln. of lactic acid | 0.40 |
| Stearyl alcohol | 3.00 |
| Highly-polymerized dimethyl polysiloxane (viscosity: 10 million cp) | 0.20 |
| Cyclic silicone* | 1.00 |
| Isononyl isononanoate | 0.20 |
| Polyglycerin diisostearate** | 0.20 |
| Dialkyl ($C_{12-18}$) dimethylammonium chloride | 0.05 |
| Benzalkonium chloride | 0.10 |
| Zinc pyrithione | 0.10 |
| Menthol | 0.10 |
| Glycerin | 2.00 |
| Sodium naphthalensulfonate | 0.10 |
| Hydroxyethyl cellulose | 0.30 |
| PH regulator (for adjusting pH 3.5 to 4.0) | q.s. |
| Perfume, colorant, methyl paraben | q.s. |
| Purified water | balance |
| Total | 100.0 |

*"SH245" (product of Toray Dow Corning Silicone Co., Ltd.)
**"Cosmol 42" (product of The Nisshin Oil Mills, Ltd.)

The hair rinse thus obtained was good in oily feel, suppleness, and smoothness from its application until rinsing, and also suppleness and smoothness after drying.

Example 9

A leave-on treatment having the following composition was prepared.

| | (wt. %) |
|---|---|
| Amine 3 | 0.60 |
| 90% Aq. soln. of lactic acid | 0.20 |

-continued

| | (wt. %) |
|---|---|
| Cetanol 1 | 1.00 |
| Highly-polymerized dimethyl polysiloxane emulsion* | 1.00 |
| Amodimethicone emulsion** | 0.50 |
| Isostearyl pentaerythryl glyceryl ether | 0.10 |
| Oxybenzenesulfonic acid | 0.05 |
| Ethanol | 5.00 |
| PH regulator (for adjusting pH 4.0 to 4.5) | q.s. |
| Perfume, methyl paraben | q.s. |
| Purified water | Balance |
| Total | 100.00 |

*"BY22-020" (product of Toray Dow Corning Silicone Co., Ltd.)
**"SM-8704C" (product of Toray Dow Corning Silicone Co., Ltd.)

A sufficient amount of the leave-on treatment thus obtained was applied to the hair which had been shampooed and therefore been wet. The treatment was not washed off.

The hair was good in finger passing or combing ease even after towel drying and also good in suppleness and smoothness after drying.

Example 10

A conditioning shampoo having the following composition was prepared.

| | (wt. %) |
|---|---|
| Amine 3 | 1.00 |
| 90% Aq. soln. of lactic acid | 0.30 |
| Sodium polyoxyethylene (2) lauryl ether sulfate | 10.00 |
| Sodium lauryl sulfate | 3.00 |
| Coconut fatty acid monoethanolamide | 1.00 |
| Lauryl amidopropylbetaine | 3.00 |
| 2-alkyl-N-carboxymethyl-N-hydroxyethyl-imidazolinium betaine | 0.50 |
| Polyoxyethylene (16) lauryl ether | 2.00 |
| Cetyltrimethylammonium chloride | 0.20 |
| Cationized cellulose* | 0.20 |
| Cationized guar gum** | 0.20 |
| Ethylene glycol distearate | 2.00 |
| Myristyl alcohol | 0.50 |
| Highly polymerized dimethylpolysiloxane emulsion*** | 2.00 |
| Amodimethicone emulsion**** | 0.50 |
| Glycerin | 1.00 |
| Ethanol | 2.00 |
| Benzyloxyethanol | 0.10 |
| Highly polymerized polyethylene glycol***** | 0.05 |
| BHT | 0.01 |
| PH regulator (for adjusting pH 5.5 to 6) | q.s. |
| Perfume, colorant, sodium benzoate | q.s. |
| Purified water | Balance |
| Total | 100.00 |

*Polymer "JR400" (product of UCC)
***"RHABALL Gum CG-M7" (product of Dainippon Pharmaceutical)
****"BY22-034" (product of Toray Dow Corning Silicone Co., Ltd.)
*****"SM-8704C" (product of Toray Dow Corning Silicone Co., Ltd.)
******"POLYOX WSR-N60K" (product of Dow Chemical Japan)

Example 11

A hair cream having the below-described composition was prepared.

| | (wt. %) |
|---|---|
| Amine 3 | 0.20 |
| Cetyltrimethylammonium chloride | 0.10 |
| 90% Aq. soln. of lactic acid | 0.10 |
| Cetanol 1 | 2.50 |
| Dimethylpolysiloxane (500 cs) | 1.00 |
| Isostearyl glyceryl ether | 0.50 |
| Glycerin | 15.00 |
| Polyoxyethylene (23) lauryl ether | 1.00 |
| Light liquid isoparaffin | 5.00 |
| Isopropyl myristate | 5.00 |
| Ethanol | 5.00 |
| PH regulator | q.s. |
| Perfume, methyl paraben | q.s. |
| Purified water | Balance |
| Total | 100.00 |

Examples 12 to 14

Hair foams each having the composition as shown below in Table 5 were prepared.

TABLE 5

| | | (wt. %) | | |
|---|---|---|---|---|
| | | Example 12 | Example 13 | Example 14 |
| Undiluted solution | Amine 3 | 0.10 | 0.10 | 0.10 |
| | 90% aq. soln. of lactic acid | 0.10 | 0.10 | 0.10 |
| | Ethanol | 15.00 | 15.00 | 15.00 |
| | Polyoxyethylene (20) isocetyl alcohol | 1.00 | 1.00 | 1.00 |
| | Vinyl pyrrolidone•N,N-dimethylaminoethylmethacrylic acid copolymer diethyl sulfate * | 1.50 | — | — |
| | Polyvinyl pyrrolidone ** | 0.20 | 0.20 | 0.20 |
| | N-methacryloyloxyethyl-N,N-dimethylammonium-α-N-methylcarboxybetaine•alkyl methacrylate copolymer solution *** | — | 2.00 | — |
| | Acrylic resin alkanolamine solution **** | — | — | 2.00 |
| | Highly polymerized dimethylpolysiloxane emulsion ***** | 2.00 | 2.00 | 2.00 |
| | Glycerin | 5.00 | 5.00 | 5.00 |
| | Polyoxyethylene tridecyl ether | 0.50 | 0.50 | 0.50 |
| | Carrageenan | 1.00 | 1.00 | 1.00 |
| | PH regulator | q.s. | q.s. | q.s. |
| | Perfume, methyl paraben | q.s. | q.s. | q.s. |
| | Purified water | Balance | Balance | Balance |
| Propellant | | 10.00 | 10.00 | 10.00 |
| LPG | | | | |
| Total | | 100.00 | 100.00 | 100.00 |

* "Gafquat 755N" (product of ISP)
** "Luviskol K80" (product of BASF)
*** "Yukafoamer R205S" (product of Mitsubishi Chemical)
**** "Diahold LP501" (product of Mitsubishi Chemical)
***** "BY22-034" (product of Toray Dow Corning Silicone Co., Ltd.)

Example 15

A hair lotion having the following composition was prepared.

|  | (wt. %) |
|---|---|
| Amine 3 | 0.20 |
| 90% Aq. soln. of lactic acid | 0.10 |
| Ethanol | 15.00 |
| Carboxyvinyl polymer * | 0.20 |
| Polyoxyethylene (60) hydrogenated castor oil | 0.50 |
| Highly polymerized polyethylene glycol ** | 0.01 |
| Menthol | 0.02 |
| Trimethylglycine | 0.10 |
| PH regulator | q.s. |
| Perfume, methyl paraben | q.s. |
| Purified water | Balance |
| Total | 100.00 |

* "Carbopol 980" (product of Noveon Inc.)
** "POLYOX WSR-N60K" (product of Dow Chemical Japan)

The hair lotion thus prepared was good in suppleness and smoothness without impairing hair setting property.

Examples 16 and 17

Hair treatments each having the composition as shown below in Table 6 were prepared.

TABLE 6

|  | (wt. %) | |
|---|---|---|
|  | Example 16 | Example 17 |
| Amine 3 | 2.00 | 4.00 |
| 50% aq. soln. of malic acid | 1.00 | 1.00 |
| 90% aq. soln. of lactic acid | 1.50 | 2.00 |
| Stearyl alchol | 5.50 | 10.00 |
| Benzyloxyethanol | 1.00 | 0.50 |
| Benzyl alcohol | — | 0.50 |
| Phenoxyethanol | — | 0.10 |
| Polypropylene glycol (molecular weight: 400) | 1.50 | — |
| Dipropylene glycol | 2.00 | 5.00 |
| Propylene carbonate | — | 0.10 |
| γ-butyrolactone | 0.20 | — |
| N-methylpyrrolidone | — | 0.10 |
| Highly polymerized dimethylpolysiloxane (viscosity: 10 million cp) | 0.50 | 1.00 |
| Dimethylpolysiloxane (viscosity: 500 cs) | 1.50 | 3.00 |
| Aminoethylaminopropylmethyl-siloxane•dimethylsiloxane copolymer (viscosity: 1000 cs, amino equivalent: 2000) | 0.05 | 0.10 |
| Isopropyl palmitate | 1.00 | 1.50 |
| Oleic acid | 0.10 | — |
| Hydrolyzed silk solution (25%) | — | 0.50 |
| PH regulator (for adjusting pH 2.8 to 4.0) | q.s. | q.s. |
| Perfume, colorant, methyl paraben | q.s. | q.s. |
| Purified water | Balance | Balance |
| Total | 100.00 | 100.00 |

The hair treatments thus prepared were good in oily feel, suppleness, smoothness from its application until after rinsing, and suppleness and smoothness after drying, and at the same time, excellent in luster after drying and had effects for preventing lift-up of cuticles of the damaged hair.

INDUSTRIAL APPLICABILITY

The conditioner compositions of the present invention can impart fiber or hair with good suppleness and smoothness during wetting and after drying. They are particularly excellent in smoothness after drying. When they are used for hair, they impart the hair with good suppleness and smoothness both before and after drying and in addition, with excellent oily feel (rich feel) during wetting.

What is claimed is:

1. A conditioner composition, which comprises:
   a tertiary amine represented by the following formula (1):

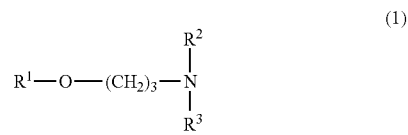

(1)

wherein, $R^1$ represents a linear or branched $C_{6-24}$ alkyl or alkenyl group, $R^2$ and $R^3$ are the same or different and each represents a $C_{1-6}$ alkyl group or $-(AO)_nH$ (in which a represents a $C_{2-4}$ alkylene group, and n is an integer from 1 to 6, wherein individual A radicals are the same or different and are arranged in any order): or a salt thereof;

(c) an oily component; and water.

2. The conditioner composition according to claim 1, wherein $R^2$ and $R^3$ each represents a $C_{1-6}$ alkyl group.

3. The conditioner composition according to claim 1, further comprising at least one compound selected from inorganic acids and organic acids.

4. The conditioner composition according to claim 2, further comprising at least one compound selected from inorganic acids and organic acids.

5. The conditioner composition according to claim 3, wherein the mole ratio of the at least one inorganic acid or organic acid to the tertiary amine ranges from 0.1 to 10.

6. The conditioner composition according to claim 1, further comprising (d) a quaternary ammonium salt.

7. The conditioner composition according to claim 3, further comprising (d) a quaternary ammonium salt.

8. The conditioner composition of claim 3, further comprising a surfactant other than said tertiary amine or a salt thereof.

9. The conditioner composition according to claim 6, further comprising a surfactant other than said tertiary amine or a salt thereof or said quaternary ammonium salt.

10. A hair cosmetic composition comprising a conditioner composition according to claim 1.

11. The conditioner composition according to claim 3, wherein the inorganic acid is at least one selected from the group consisting of hydrochloric acid, phosphoric acid or sulfuric acid and said organic acid is at least one selected from the group consisting of a monocarboxylic acid, a dicarboxylic acid, a hydroxycarboxylic acid, a polycarboxylic acid or an amino acid.

12. The conditioner composition according to claim 1, which has a pH ranging from 2 to 8.

13. The conditioner composition according to claim 6, wherein said quaternary ammonium salt has the formula:

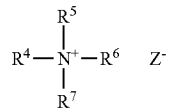 (5)

wherein at least one of $R^4$, $R^5$, $R^6$ and $R^7$ is a linear or branched alkyl or alkenyl group that is optionally substituted by alkoxy, alkenyloxy, alkanoylamino, alkenoylamino, alkanoyloxy or alkenoyloxy, each containing from 12 to 28 carbon atoms and the remaining groups are benzyl, $C_{1-5}$ alkyl, hydroxyalkyl or polyoxyethylene whose added molar number is not more than 10.

14. The conditioner composition according to claim 6, wherein the weight ratio of tertiary amine to quaternary ammonium salt is 1/4 to 20/1.

15. The conditioner composition according to claim 1, which, other than the tertiary amine, further comprises at least one cationic, anionic, nonionic or amphoteric surfactant in an amount which does not impair the function of the tertiary amine on the hair.

16. The conditioner composition according to claim 1, which further comprises a thickener of a cationic copolymer in an amount of 0.01 to 20 wt % based on the weight of the conditioner composition.

17. The conditioner composition according to claim 1, which further comprises a thickening polymer in an amount of 0.01 to 20 wt % based on the weight of the conditioner composition.

18. The conditioner composition according to claim 1, wherein said oily component is present in an amount of 0.01 to 30 wt % based on the weight of the conditioner.

19. The conditioner composition according to claim 1, wherein the oily component is a higher alcohol, an ester oil, a silicone, a light liquid isoparaffin, a light liquid paraffin, paraffin, wax, squalane or a glyceride.

20. The conditioner composition of claim 1, wherein said composition is the result of mixing said tertiary amine with at least one compound selected from the group consisting of inorganic acids and organic acids.

* * * * *